US010555752B2

(12) United States Patent
Robertson et al.

(10) Patent No.: US 10,555,752 B2
(45) Date of Patent: Feb. 11, 2020

(54) ROTATIONAL MECHANICAL THROMBECTOMY DEVICE

(71) Applicant: TELEFLEX MEDICAL INCORPORATED, Morrisville, NC (US)

(72) Inventors: Taylor Robertson, Sinking Spring, PA (US); Brian K. Roth, Wyomissing, PA (US); Wade K. Trexler, Coopersburg, PA (US); Richard E. Bohn, Leesport, PA (US); David Rowe, Fleetwood, PA (US); Rodney Wilmer Denlinger, Lancaster, PA (US); Eugene Skelton, Dublin (IE); Anthony Wright, Co. Waterford (IE); Ronan Benson, Dublin (IE)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 163 days.

(21) Appl. No.: 15/426,137

(22) Filed: Feb. 7, 2017

(65) Prior Publication Data

US 2017/0224375 A1    Aug. 10, 2017

Related U.S. Application Data

(60) Provisional application No. 62/292,452, filed on Feb. 8, 2016.

(51) Int. Cl.
*A61B 17/3207* (2006.01)
*A61B 17/00* (2006.01)

(52) U.S. Cl.
CPC ........ *A61B 17/320758* (2013.01); *A61B 17/320725* (2013.01); *A61B 2017/0046* (2013.01);
(Continued)

(58) Field of Classification Search
CPC .... A61B 17/320758; A61B 17/320725; A61B 2017/00973; A61B 2017/00734;
(Continued)

(56) References Cited

U.S. PATENT DOCUMENTS 5,849,023 A    12/1998  Mericle
6,019,772 A *   2/2000  Shefaram ....... A61B 17/320758
                                                606/159

(Continued)

*Primary Examiner* — David C Eastwood
(74) *Attorney, Agent, or Firm* — Baker & Hostetler LLP

(57) ABSTRACT

The present disclosure relates to a mechanical thrombectomy device that includes a catheter assembly with a basket assembly formed of a proximal hub and a distal hub; a flexible tube having a first end attached to the proximal hub and a second end attached to the distal hub; and a plurality of basket wires. The flexible tube may be laser-cut to allow for bending, elongation, and compression. The basket wires each have a first end attached to the proximal hub and a second end attached to the distal hub. The basket wires are disposed around the flexible tube and configured to expand to a preset shape. The basket assembly is attached to a distal end of a rotatable shaft. A drive assembly is configured to rotate the rotatable shaft to rotate the basket assembly. The basket assembly when rotated is configured to macerate a material proximate to the basket assembly.

20 Claims, 22 Drawing Sheets

(52) U.S. Cl.
CPC ........... *A61B 2017/00367* (2013.01); *A61B 2017/00424* (2013.01); *A61B 2017/00734* (2013.01); *A61B 2017/320733* (2013.01); *A61B 2017/320775* (2013.01); *A61B 2217/007* (2013.01)

(58) Field of Classification Search
CPC ......... A61B 2017/00424; A61B 2017/320733; A61B 2017/0046; A61B 2017/320775; A61B 2017/00367; A61B 2217/007
See application file for complete search history.

(56) References Cited

U.S. PATENT DOCUMENTS

| | | | | |
|---|---|---|---|---|
| 6,235,042 B1* | 5/2001 | Katzman | ........ | A61B 17/320758 606/159 |
| 2001/0031981 A1* | 10/2001 | Evans | ........ | A61B 17/221 606/200 |
| 2002/0058961 A1* | 5/2002 | Aguilar | ........ | A61M 29/02 606/198 |
| 2008/0009877 A1* | 1/2008 | Sankaran | ........ | A61B 17/1617 606/84 |
| 2008/0208230 A1* | 8/2008 | Chin | ........ | A61B 17/1617 606/167 |
| 2008/0262476 A1 | 10/2008 | Krause et al. | | |
| 2009/0018567 A1* | 1/2009 | Escudero | ........ | A61B 17/320758 606/159 |
| 2010/0317995 A1* | 12/2010 | Hibner | ........ | A61B 10/0275 600/564 |
| 2012/0109171 A1 | 5/2012 | Zeroni et al. | | |
| 2014/0094841 A1* | 4/2014 | Sutton | ........ | A61B 17/221 606/200 |
| 2014/0222042 A1* | 8/2014 | Kessler | ........ | A61B 17/320783 606/159 |
| 2014/0277041 A1* | 9/2014 | Manley | ........ | A61B 17/32002 606/170 |
| 2015/0150587 A1* | 6/2015 | Smith | ........ | A61B 17/32002 606/159 |
| 2016/0120569 A1* | 5/2016 | Kobayashi | ........ | A61B 90/39 606/159 |
| 2016/0270813 A1* | 9/2016 | Chida | ........ | A61B 17/320758 |
| 2016/0287283 A1* | 10/2016 | Vetter | ........ | A61F 2/013 |
| 2016/0354107 A1* | 12/2016 | Nakano | ........ | A61B 17/320725 |
| 2016/0354108 A1* | 12/2016 | Nakano | ........ | A61B 17/320758 |
| 2016/0374714 A1* | 12/2016 | Majercak | ........ | A61B 17/320725 606/159 |
| 2017/0020556 A1* | 1/2017 | Sutton | ........ | A61B 17/320758 |
| 2017/0189056 A1* | 7/2017 | Nakano | ........ | A61B 17/320758 |

* cited by examiner

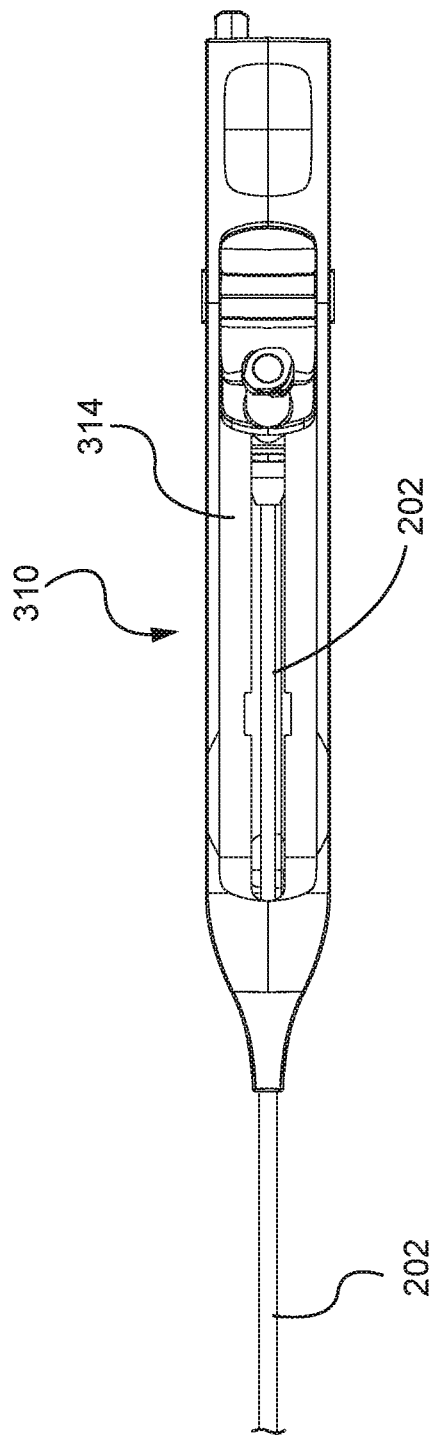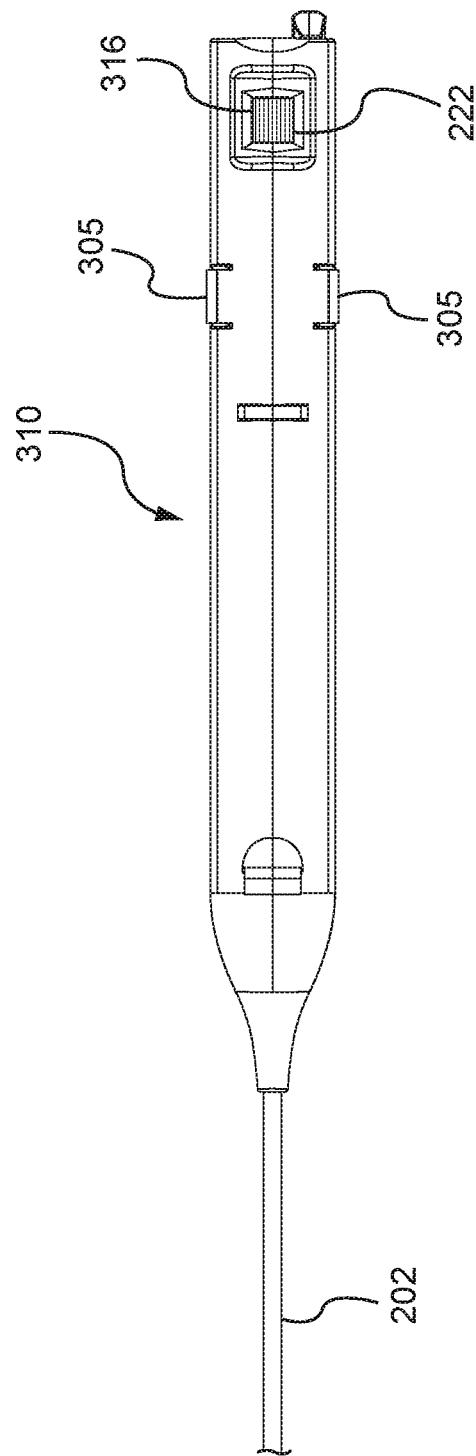
FIG. 14
FIG. 15

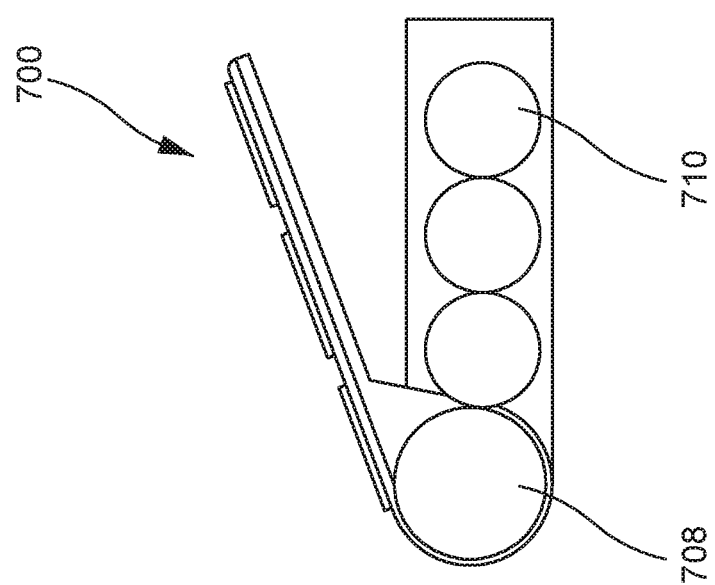

ROTATIONAL MECHANICAL THROMBECTOMY DEVICE

RELATED APPLICATIONS

This application claims priority to U.S. Provisional Patent Application No. 62/292,452, filed Feb. 8, 2016, the contents of which are hereby incorporated in its entirety by reference.

TECHNICAL FIELD

This application relates generally to a mechanical thrombectomy device and, more specifically, to a thrombectomy device that uses a rotating basket assembly to macerate blood clots.

BACKGROUND ART

Venous thromboembolism (VTE), including deep vein thrombosis (DVT) and pulmonary embolism (PE), is a common cardiovascular disorder that affects up to 2 million patients in the U.S. each year. VTE is a significant risk in surgical patient populations where preoperative, operative, and postoperative immobilization may lead to blood stasis. VTE, when poorly treated, may lead to the development of post-thrombotic syndrome (PTS), with symptoms including chronic leg pain, swelling, and ulcers. As a consequence of PTS, many individuals struggle with a reduced quality of life.

Current treatment options for VTE include anticoagulation, catheter-direct thrombolysis (CDT) and pharmacomechanical thrombectomy. However, the efficacy of these methods is disputed. One deficiency of these methods is the use of thrombolytic agents, which may present a risk of internal bleeding, including the potential for an intracranial bleeding event. In particular, such agents are effective because they cause blood thinning and prevent coagulation. However, their use can cause bleeding complications. The use of methods involving thrombolytic agents may also be ineffective to treat against blood clots in larger veins, such as veins located in a patient's leg. Many thrombolytic agents are also costly, and logistically complicated to use.

As an alternative, mechanical compression devices that compress or squeeze portions of a patient's body to force blood flow have been used. But such devices include their own drawbacks. Oftentimes, these kinds of devices are bulky and may impose a considerable burden on hospital staff. Patients are also less inclined to ambulate while using these devices because they typically are burdensome to remove and reapply. Many patients also dislike using mechanical compression systems because such devices are typically uncomfortable. In addition, these kinds of compression devices also may not be effective at treating thrombosis in larger veins.

Accordingly, there is a need for a device that is designed to effectively treat thrombosis in large veins without using thrombolytic agents.

SUMMARY OF THE DISCLOSURE

The foregoing is met, to a great extent, by a mechanical thrombectomy device that uses a rotating, self-expanding basket assembly to macerate blood clots. The basket assembly is designed to contact its surroundings, and therefore reduces a need for using thrombolytic agents or lytics. The basket assembly may be optimized for use in large peripheral veins. The device may include a flexible metallic center lumen that allows it to be used over a standard size guidewire. The device may also include additional features that facilitate easy operation, including a cartridge design that allows the catheter to be disconnected from a drive assembly, as well as two actuation mechanisms (e.g., a hand trigger and a foot pedal).

In an aspect, a mechanical thrombectomy device includes a catheter assembly and a drive assembly. The catheter assembly includes a rotatable shaft having a proximal end and a distal end, and a basket assembly attached to the distal end of the rotatable shaft. The basket assembly includes a proximal hub and a distal hub disposed on a longitudinal axis of the basket assembly; a flexible inner tube having a first end attached to the proximal hub and a second end attached to the distal hub; and a plurality of basket wires. The flexible inner tube includes perforations such that the flexible inner tube and the basket assembly can expand axially and twist rotationally along the longitudinal axis. The plurality of basket wires each have a first end attached to the proximal hub and a second end attached to the distal hub. The plurality of basket wires are disposed around the flexible inner tube and configured to expand to a preset shape. The drive assembly is configured to rotate the rotatable shaft, which in turn rotates the basket assembly. The basket assembly when rotated is configured to macerate a material proximate to the basket assembly.

There are, of course, additional aspects of the disclosure that will be described below and which will form the subject matter of the claims. In this respect, before explaining at least one aspect of the disclosure in detail, it is to be understood that the disclosure is not limited in its application to the details of construction and to the arrangements of the components set forth in the following description or illustrated in the drawings. The disclosure is capable of aspects in addition to those described and of being practiced and carried out in various ways. Also, it is to be understood that the phraseology and terminology employed herein, as well as the Abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the disclosure. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the disclosure are illustrated by way of examples in the accompanying drawings.

FIG. 14 is a top perspective view of the cartridge assembly depicted in FIG. 11.

FIG. 15 is a bottom perspective view of the cartridge assembly depicted in FIG. 11.

FIG. 25 is a cross-sectional view of the foot actuation mechanism depicted in FIG. 24.

Aspects of a mechanical thrombectomy device according to aspects of the disclosure are described with reference to the drawings, in which like reference numerals refer to like parts throughout.

DETAILED DESCRIPTION

Systems and methods disclosed herein provide a mechanical thrombectomy device designed to treat deep vein thrombosis. The mechanical thrombectomy device may be designed to effectively work in large veins without using lytics. The device may be a single-use, handheld device that is capable of removing wall adherent and intraluminal clots via rotary maceration. The device is designed to work over a standard size guidewire and, specifically, includes a flexible metallic center lumen that is capable of sliding over a guidewire. The device also includes wall contact features, including a macerating basket that is designed to directly contact and macerate material forming a blood clot. This wall contact design allows the device to be used without lytics or with a reduced amount of lytics. The device may also include user-friendly features, including a cartridge design that facilitates easy connection and separation of a catheter from a handle assembly, as well as two actuator options (e.g., a hand trigger and a foot pedal). The mechanical thrombectomy device according to systems and methods described herein may be used for venous thrombectomy, arterial thrombectomy, and pulmonary thrombectomy.

Systems and methods disclosed herein also disclose a rotating, self-expanding basket for macerating blood clots. The basket may be disposed at the distal end of a catheter assembly of a mechanical thrombectomy device. The basket may be rotated via a battery-powered motor that is connected to the basket through a gear train and a torque cable. The battery, motor, and gear train may be housed within a handle assembly. The handle assembly may also include a trigger (e.g., a first actuator) and a connector for a foot pedal (e.g., a second actuator). The basket and handle may be designed to work with a guidewire, such as a commercially available 0.035 inch guidewire.

Figure 1:
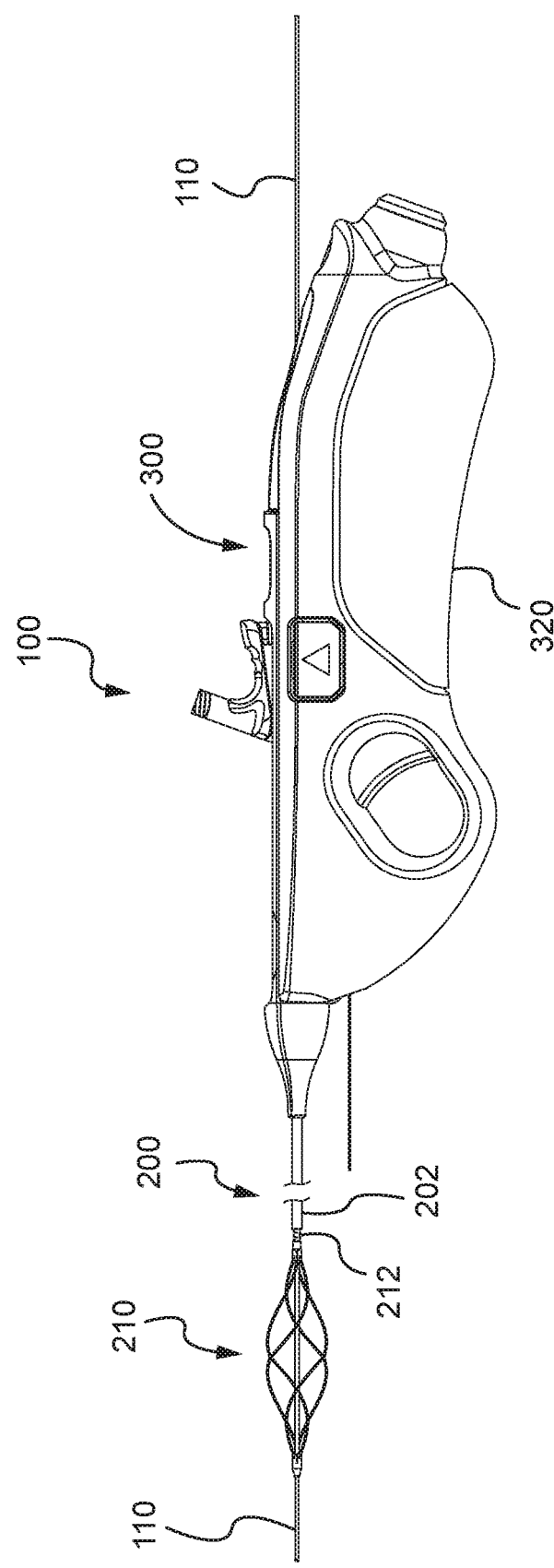
FIG. 1 is a side perspective view of an example mechanical thrombectomy device according to an aspect of the disclosure.

Referring now to FIG. 1, a side view of an example mechanical thrombectomy device 100 is illustrated. The mechanical thrombectomy device 100 includes a catheter assembly 200 and a drive assembly 300. The catheter assembly 200 includes a basket assembly 210 at its distal end. A proximal end of the catheter assembly may be enclosed in a cartridge assembly (depicted in later figures), which is attached to a top portion of the handle assembly 320. The catheter assembly 200 further includes an outer sheath 202 and a torque cable 212. The basket assembly 210, as depicted in FIG. 1, is attached to a distal end of the torque cable 212. The catheter assembly 200 may be introduced over a guidewire 110 into an intraluminal space such as, for example, a blood vessel.

Figure 2:
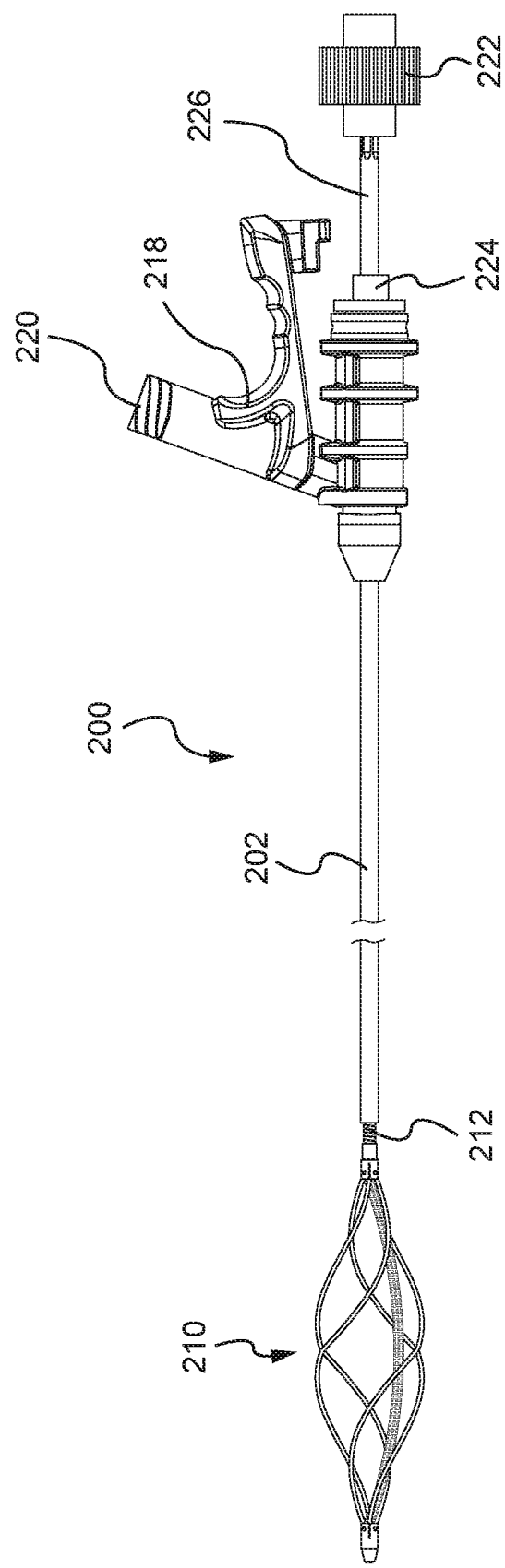
FIG. 2 is a side perspective view of an example catheter assembly of a mechanical thrombectomy device according to an aspect of the disclosure.

FIG. 2 provides a more detailed view of the catheter assembly 200. As depicted in FIG. 2, the catheter assembly 200 includes an outer sheath 202, a torque cable 212, a basket assembly 210, a slider 218, an infusion inlet 220, a valve cap 224, a stiffening cannula 226, and a drive gear 222. The torque cable 212 may include a metal center that is coated with a polymer material. For example, the torque cable 212 may be a stainless steel cable that is covered with a thin layer of polytetrafluoroethylene (PTFE) shrink wrap. The torque cable 212 may be flexible and include a center lumen. The torque cable 212 may be disposed within an outer sheath 202. The torque cable 212 may be an example of a rotatable shaft. The outer sheath 202 may be an example of a sheath. The outer sheath 202 may provide insulation between the torque cable 212 and a vessel wall.

Figure 4:
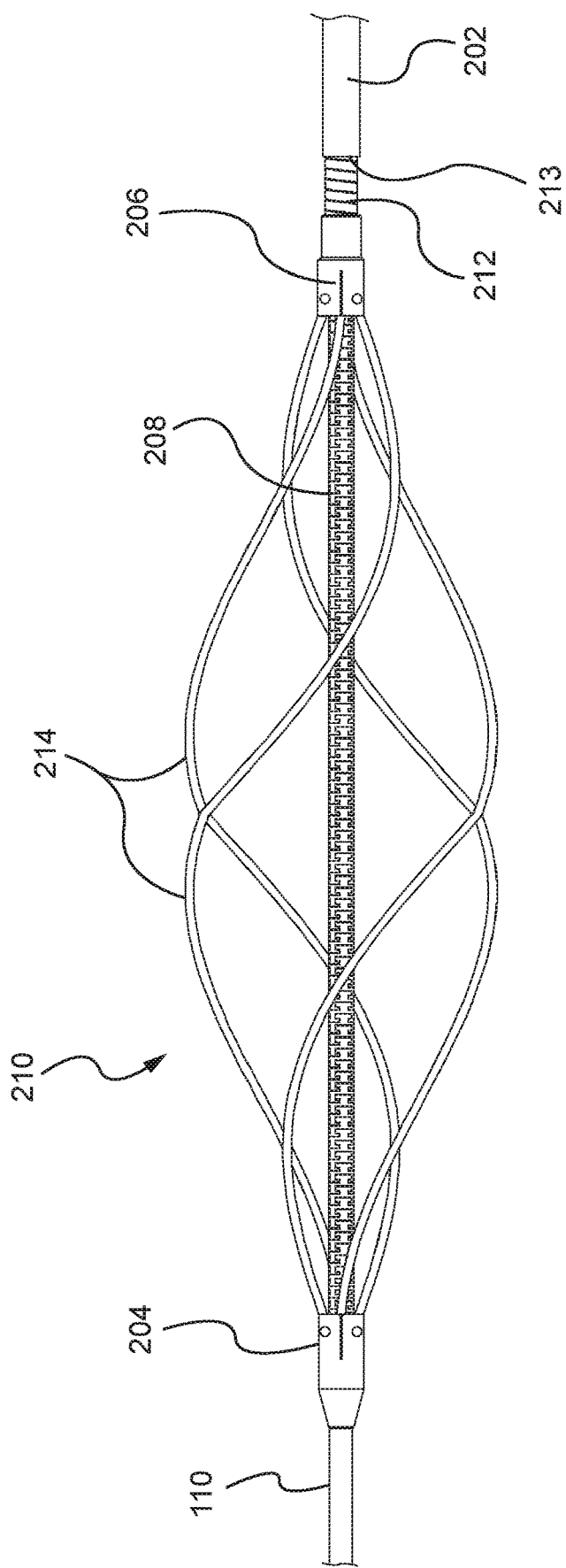
FIG. 4 is a side perspective view of a distal end of the catheter assembly depicted in FIG. 2, showing an expanded basket assembly with a guidewire extending through a center lumen of the basket assembly.

A gap between the torque cable 212 and the outer sheath 202 (e.g., a space between an outside surface of the torque cable 212 and the inside surface of the outer sheath 202) may provide an annular space for infusion of liquids, such as fluoroscopy contrast agents or lytics. This gap is shown in FIG. 4 as item 213. The outer sheath 202 may include a radiopaque distal tip. A proximal end of the outer sheath 202 may be attached to the slider 218. The slider 218 may be an example of a retracting mechanism. The slider 218 may include a luer port. The luer port may define an infusion inlet 220 that provides access to the infusion lumen 213. The valve cap 224, including an internal sealing portion, may prevent leakage of fluids introduced into the infusion lumen 213 from a proximal side of the slider 218.

A proximal end of the torque cable 212 is connected to a stiffening cannula 226. The stiffening cannula 226 may provide structural support for the torque cable 212 at the region where the torque cable 212 is disposed in the stiffening cannula 226. The stiffening cannula 226 also provides a stable platform for the slider 218 to slide or translate across. The stiffening cannula 226 and the torque cable 212 are assembled into the drive gear 222.

Figure 3:
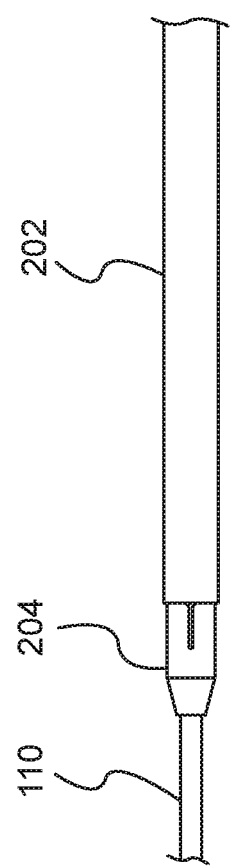
FIG. 3 is a side perspective view of a distal end of a catheter assembly depicted in FIG. 2, showing a sheath covering a basket assembly.

Referring now to FIG. 3, an enlarged view of a distal end of the catheter assembly 200 is depicted. As depicted in FIG. 3, the basket assembly 210 of the catheter assembly 200 is collapsed within the outer sheath 202. The catheter assembly 200 with the basket assembly 210 collapsed may be inserted into a body lumen over a guidewire 110. The distal end of the catheter assembly 200, including the basket assembly 210, may be guided in the body lumen until the basket assembly 210 reaches the location of a blood clot, which may be determined using imaging technology. Once the distal end of the catheter assembly 200 is in position, the outer sheath 202 may be pulled back to allow the basket assembly 210 to expand to a preset shape. The outer sheath 202 may be pulled back via an actuation of the slider 218. Specifically, the slider 218 may be pulled back along the stiffening cannula 226 such that the outer sheath 202 is pulled back a required length to expose the basket assembly 210.

As depicted in FIG. 4, the basket assembly 210 may comprise a distal hub 204, a proximal hub 206, a center flexible inner tube 208, and a plurality of basket wires 214. The plurality of basket wires 214 may be formed of self-expanding material that is set to expand to a predetermined shape. Specifically, the plurality of basket wires 214 may be formed of a metal that is heat set to expand to a particular shape. According to a preferred aspect of the disclosure, the basket assembly 210 is formed of metallic material to facilitate the joining of various parts (e.g., the basket wires 214 and the hubs 204, 206) to one another, resulting in a stronger basket design.

The diameter of the basket assembly 210 following the expansion of the basket wires 214 may be designed to treat larger veins. In its collapsed state, however, the basket assembly 210 may be designed to be inserted through a smaller vein. Depending on the particular application, the diameter of the basket assembly 210 may be scaled up or down to target different veins. In a preferred aspect of the disclosure, the basket assembly 210 may have a diameter of approximately 20 millimeters.

According to the example depicted in FIG. 4, the basket assembly 210 includes four basket wires 214. In different aspects, this number may be reduced or increased depending on the needs of a particular application. The basket wires 214 may be twisted and heat set into an expanded, helical shape. The basket wires 214 have a first end that is attached to the distal hub 204 and a second end that is attached to the proximal hub 206. The proximal hub 206 is in turn is attached to the torque cable 212. As such, a rotation of the torque cable 212 would cause a corresponding rotation of the basket assembly 210.

Figure 6:
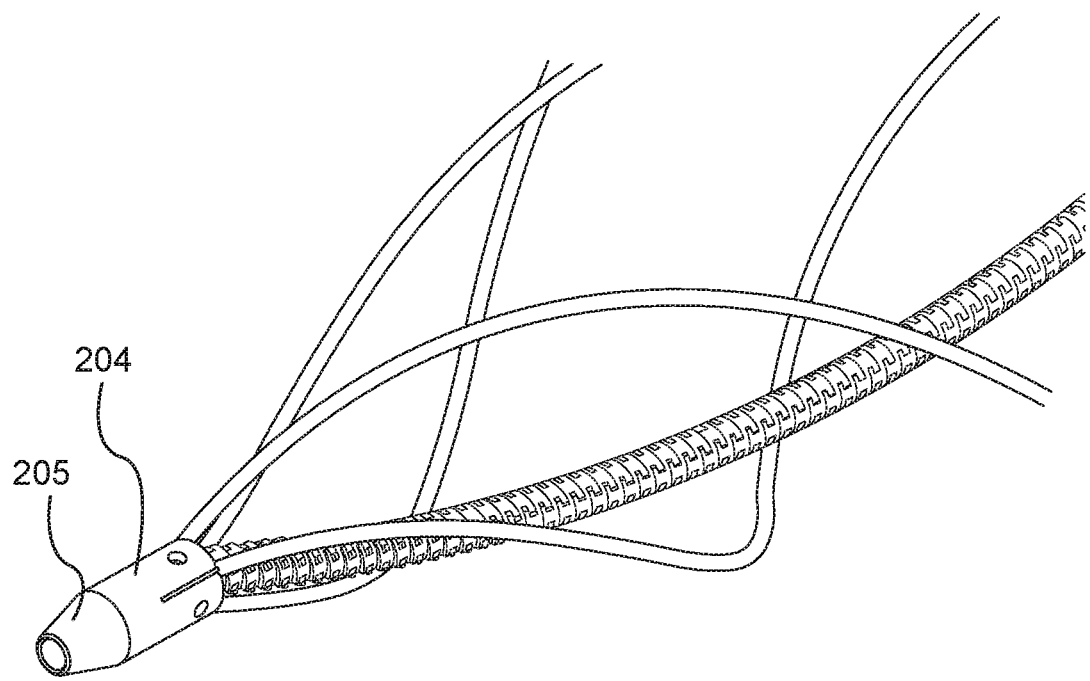
FIG. 6 is an enlarged view of a distal end of an expanded basket assembly having a smooth surface according to an aspect of the disclosure.
Figure 7:
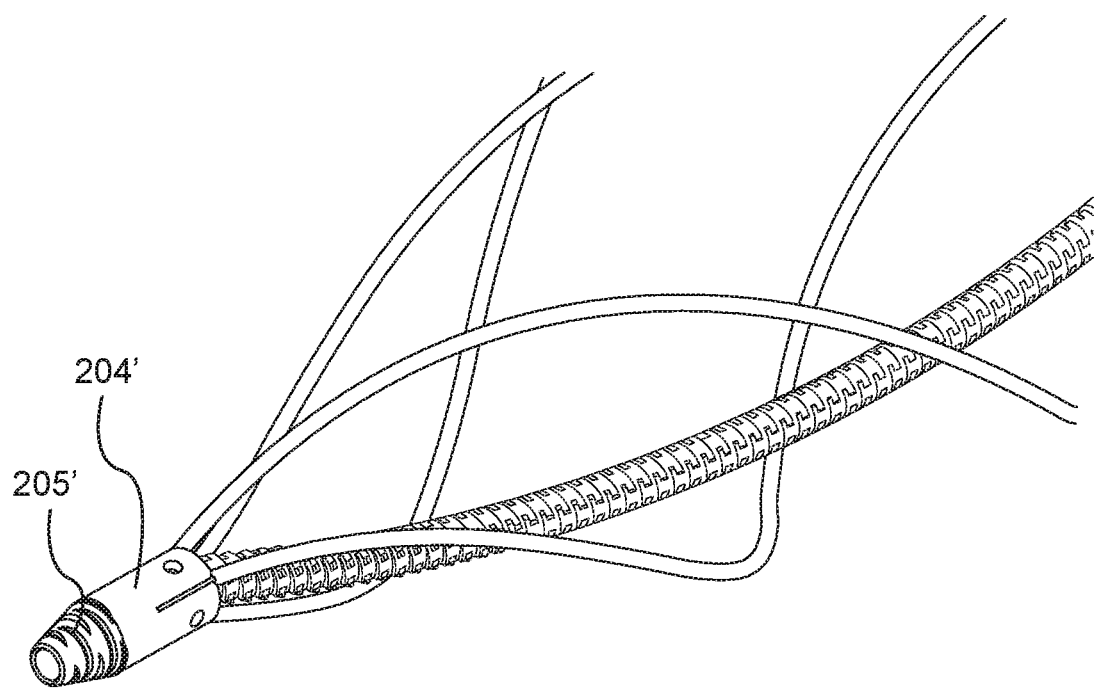
FIG. 7 is an enlarged view of a distal end of an expanded basket assembly having a cross-cut engraving according to an aspect of the disclosure.
Figure 8:
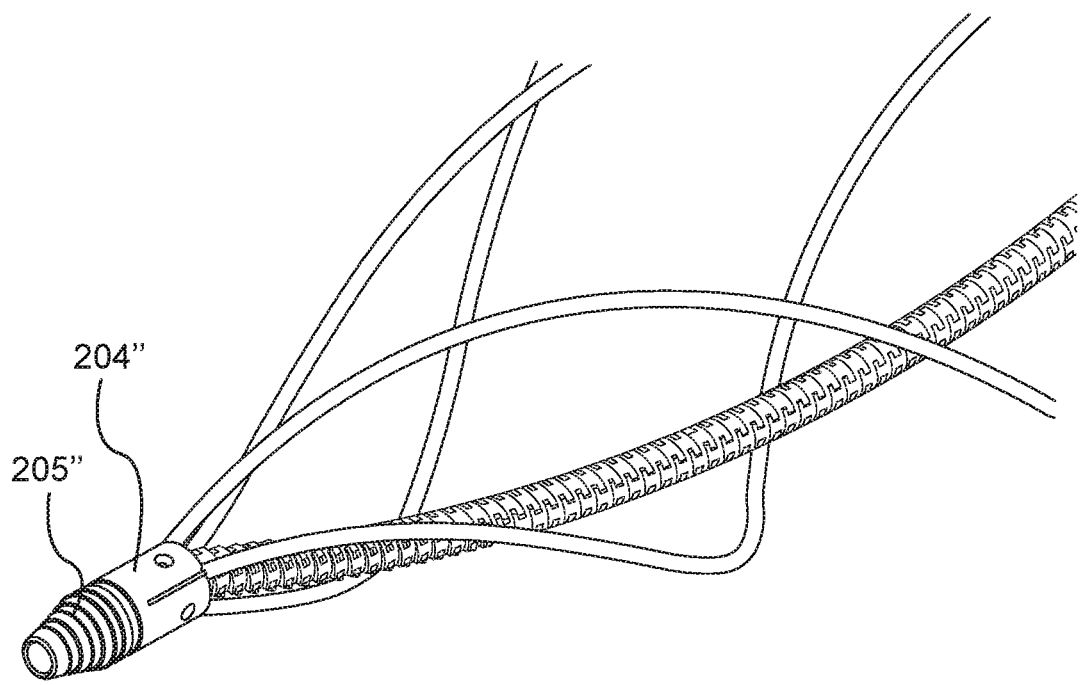
FIG. 8 is an enlarged view of a distal end of an expanded basket assembly having a concentric engraving according to an aspect of the disclosure.
Figure 9:
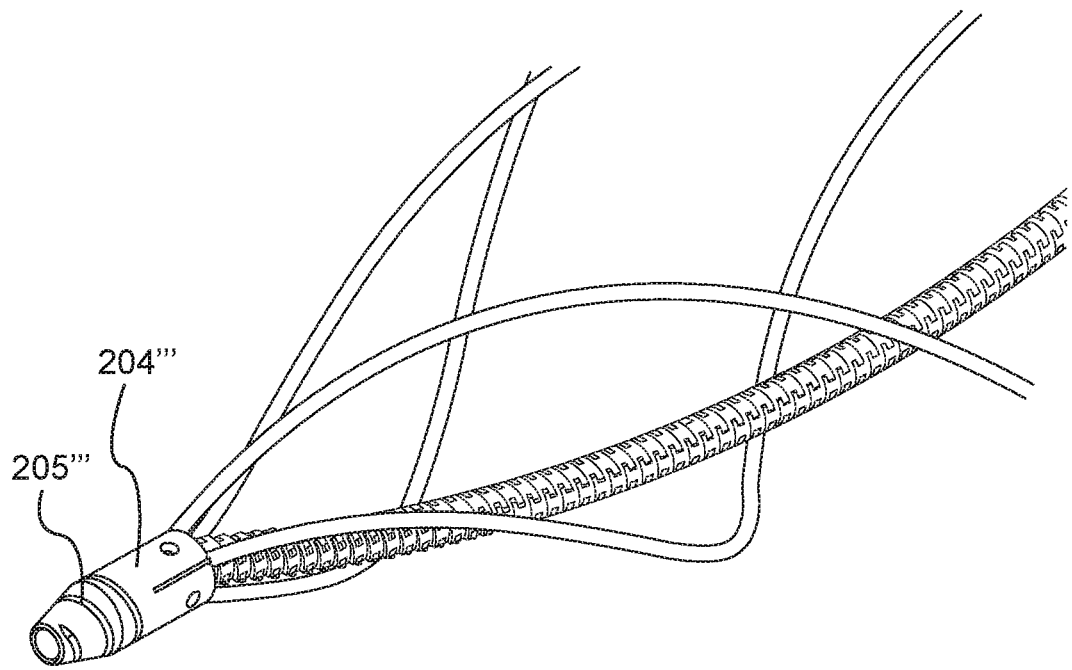
FIG. 9 is an enlarged view of a distal end of an expanded basket assembly having a spiral engraving according to an aspect of the disclosure.

The distal hub 204 of the basket assembly 210 includes a conical tip 205 (see FIG. 6). As depicted in FIG. 4, this conical tip 205 may have a smooth surface. According to alternative aspects of the disclosure, the conical tip may also include features that would facilitate the maceration of hardened blood clots by facilitating entanglement of the clot at the tip. For example, as depicted in FIGS. 7-9, the distal hub of the basket assembly may include a conical tip 205' having cross-cut engravings (see FIG. 7), a conical tip 205" having concentric engravings (see FIG. 8), and a conical tip 205''' having spiral engravings (see FIG. 9).

The center flexible inner tube 208 of the basket assembly 210 (see FIG. 4) is positioned concentrically with respect to the axis of each hub. Each end of the flexible inner tube 208 is connected to one of the hubs 204, 206, and the basket wires 214 are arranged around the axis of the flexible inner tube 208. The ends of the flexible inner tube 208 may be welded to the hubs 204, 206, and the proximal hub 206 may be welded to the torque cable 212. According to preferred aspects of the disclosure, the basket wires 214 are arranged symmetrically around the flexible inner tube 208. The flexible inner tube 208 provides guidewire alignment and support during advancement, withdrawal, and rotation of the basket assembly 210. For example, the flexible inner tube 208 may increase a user's ability to track the catheter as it is guided over the guidewire 110. The flexible inner tube 208 may also reduce the risk of losing guidewire access through the distal end of the basket assembly 210 when the catheter assembly 200 is advanced beyond the end of the guidewire. In addition, the flexible inner tube 208 may expand and contract with the expansion of the basket wires 214. As such, the flexible inner tube 208 may prevent an over-expansion of the basket wires 214. More specifically, the flexible inner tube 208 may comprise multiple independent pieces and only be compressed until adjacent pieces of the flexible inner tube 208 interfere with one another. Thus, since the flexible inner tube 208 is joined at both ends to the two hubs 204, 206, the flexible inner tube 208 limits the distance between the two hubs 204, 206, thereby limiting the expansion of the basket wires 214. Furthermore, the flexible inner tube 208 may prevent the basket assembly 210 from twisting unto itself in torsion.

Figure 10:
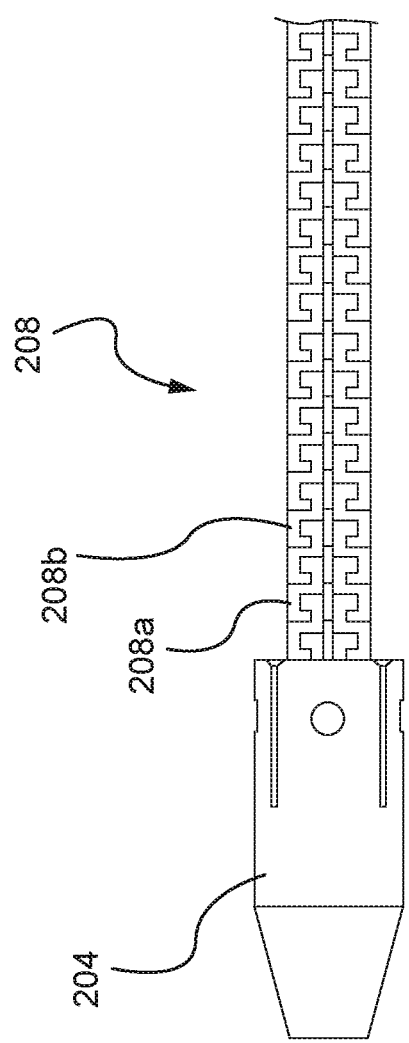
FIG. 10 is an enlarged view of a flexible inner tube of a basket assembly according to an aspect of the disclosure.

The flexible inner tube 208 may be manufactured by laser cutting a solid cannula tube into multiple independent pieces. In an aspect, the flexible inner tube 208 may be manufactured by laser cutting a jigsaw pattern into a solid hypo tube (see FIG. 10). The laser cutting is designed to create independent pieces (e.g., pieces 208a and 208b) that interlock with adjacent pieces. Thus, after the laser cutting, the cannula tube becomes flexible and is capable of bending, elongation, and rotation. In such fashion, the cannula tube also allows for elongation, compression, and rotation of the hubs 204, 206 with respect to one another. According to a preferred aspect of the disclosure, the flexible inner tube 208 is provided in a neutral configuration in which it does not force the basket wires 214 to expand or compress, or rotate the hubs 204, 206 with respect to each other (e.g., the flexible inner tube 208 is designed for neutral force displacement). Instead, in the neutral configuration, the shape of the basket assembly 210 is defined by a heat setting process and the lengths of the basket wires 214. According to other aspects of the disclosure, the flexible inner tube 208 may be designed to expand the basket wires 214, compress the basket wires 214, or cause a rotation of a first hub (e.g., distal hub 204) with respect to the other (e.g., proximal hub 206).

Figure 5:
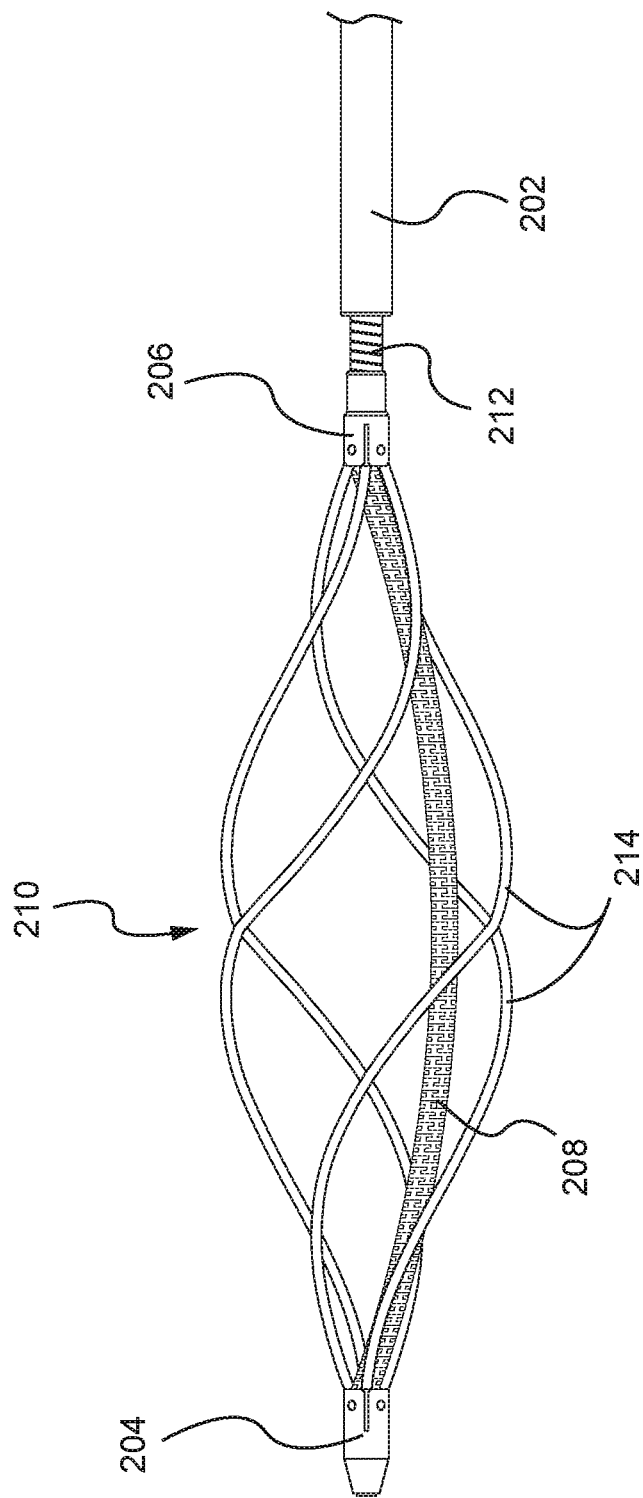
FIG. 5 is a side perspective view of a distal end of the catheter assembly depicted in FIG. 2, showing an expanded basket assembly without a guidewire.

FIG. 5 depicts the distal end of the basket assembly 210 with the guidewire 110 removed from the inner lumen of the flexible inner tube 208. Such may result when the basket assembly 210 has been advanced beyond the end of the guidewire. Alternatively, the guidewire 110 may have been withdrawn from the device. With the guidewire 110 removed, the flexible inner tube 208 may hang loosely (e.g., be floppy), as shown in FIG. 5.

Figure 11:
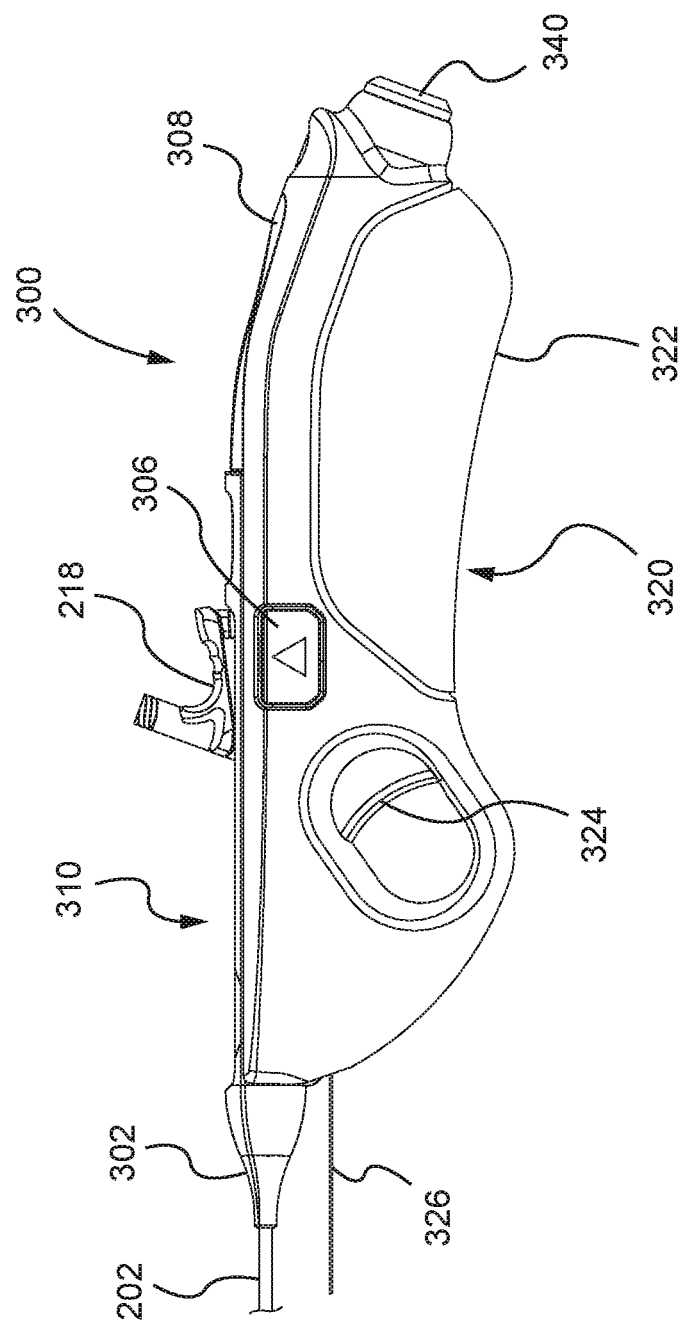
FIG. 11 is a side perspective view of an example cartridge assembly attached to a handle assembly of a mechanical thrombectomy device according to an aspect of the disclosure.

Referring now to FIG. 11, an example cartridge assembly 310 that is attached to a handle assembly 320 is illustrated. The cartridge assembly 310 and the handle assembly 320 together form a drive assembly 300. The cartridge assembly 310 may be attached to a top region of the handle assembly 320. The cartridge assembly 310 may enclose a proximal end of the catheter assembly 200 (depicted in FIG. 2), thereby fixing the position of the catheter assembly 200 with respect to the handle assembly 320.

FIGS. 13-16 provide more detailed views of the cartridge assembly 310. As depicted, the cartridge assembly 310 includes housing portions 311, 313, strain relief 302, wings 305, a pivot point 307, a spring 318, and a gear lock component 319. The housing portions 311, 313 enclose the proximal end of the catheter assembly 200, including a portion of the outer sheath 202, the slider 218, and the drive gear 222. When enclosed in the housing portions 311, 313, the slider 218 (and therefore the outer sheath 202) is capable of translating or sliding longitudinally within the cartridge assembly 310. Such may be facilitated by a window or opening 314 (see FIG. 14). As described above, such translating movement of the slider 218 is necessary to retract the outer sheath 202 and thereby allow expansion of the basket wires 214. More specifically, such translating movement allows for deployment and recapture of the basket assembly 210 by moving the distal end of the outer sheath 202 with respect to the distal end of the basket assembly 210 (see FIGS. 3 and 4). The slider 218 may include a vertical cant that contacts and provides interference with the housing portions 311, 313 of the cartridge assembly 310 throughout the majority of its translation. The cant may mate with sections of the window 314 to lock the slider 218 at each end of its translation to prevent an inadvertent translation of the slider 218.

According to certain aspects of the disclosure, the mechanical thrombectomy device 100 may additionally include proximity sensors (not depicted) that prevent the torque cable 212 and the basket assembly 210 from rotating until the slider 218 has translated a certain distance backwards (e.g., until the slider 218 has achieved some percentage of its axial travel). In some aspects, the proximity sensors may only allow the basket assembly 210 to rotate when the slider 218 is in a fully retracted position. In other aspects, the proximity sensors may prevent the basket assembly 210 from rotating until the slider 218 is retracted a certain amount that is less than a full retraction. In such aspects, the outer sheath 202 may be used to limit an expansion of the basket wires 214 when the basket assembly 210 is rotated. The strain relief 302 of the cartridge assembly 310 (see FIG. 11) may prevent kinking of the catheter assembly 200 as it moves or rotates within the cartridge assembly 310.

The cartridge assembly 310 further includes an opening 316 at its proximal end (see FIG. 15), which exposes a portion of the drive gear 222 of the catheter assembly 200. This opening 316 allows the drive gear 222 to engage with other gears (described below) which are disposed in the handle assembly 320 (see FIG. 12). The engagement between the drive gear 222 and these other gears sets up the gear train that allows a motor 334, disposed in the handle assembly 320, to drive the rotation of the torque cable 212 and, consequently, the basket assembly 210.

The cartridge assembly 310 is capable of locking to a top portion of the handle assembly 320 via a pair of wings 305 (see FIGS. 13 and 15) that snap into portions of handle locking tabs 306 (see FIG. 11) disposed on the handle assembly 320. The cartridge assembly 310 includes a pivot point 307 along its bottom face near its distal end. The cartridge assembly 310 may be attached to the handle assembly 320 by aligning this pivot point 307 with a mating feature on the handle assembly 320, and the cartridge assembly 310 is pivoted down until the wings 305 snap into place by engaging with corresponding portions of the locking tabs 306. The cartridge assembly 310 may be disconnected or separated from the handle assembly 320 by depressing the locking tabs 306 to release the wings 305. In particular, when the locking tabs 306 are depressed, they cause the wings 305 on the cartridge assembly 310 to flex inwards and push downwards on the handle assembly 320, thereby separating the two components.

According to aspects of the disclosure, the mechanical thrombectomy device 100 may be shipped to a customer with the cartridge assembly 310 attached to the handle assembly 320 (e.g., with the cartridge assembly 310 preassembled to the handle assembly 320) for ease of use. But the functionality of being able to remove the cartridge assembly 310 from the handle assembly 320 may be useful in situations where a user may need to manually unwind a portion of the device. For example, a user may want to remove the cartridge assembly 310 from the handle assembly 320 to unwind the basket assembly 210 when the basket assembly 210 becomes entangled in a stent or becomes lodged in a blood clot.

Figure 16:
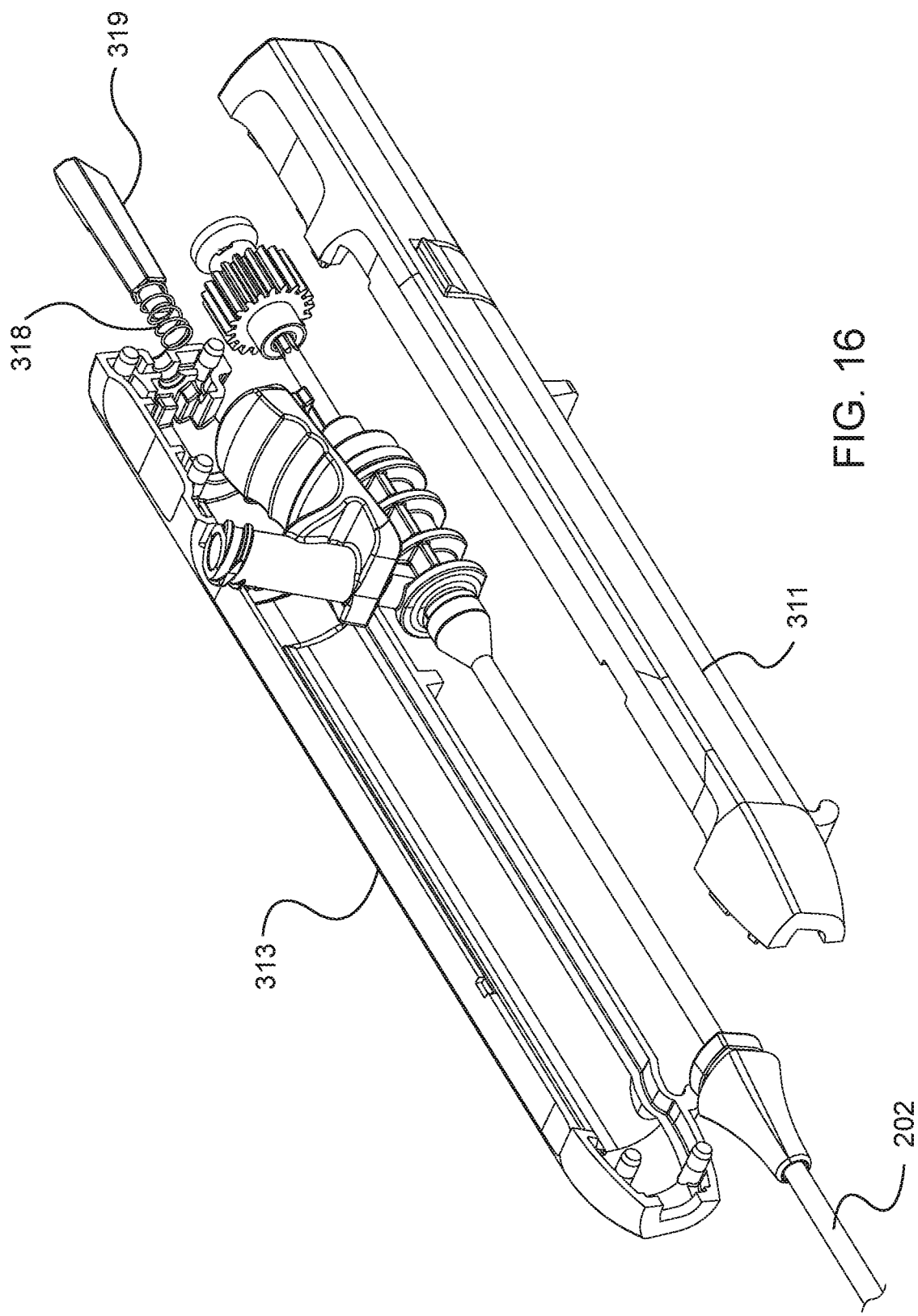
FIG. 16 is a deconstructed view of the cartridge assembly depicted in FIG. 11.
Figure 17:
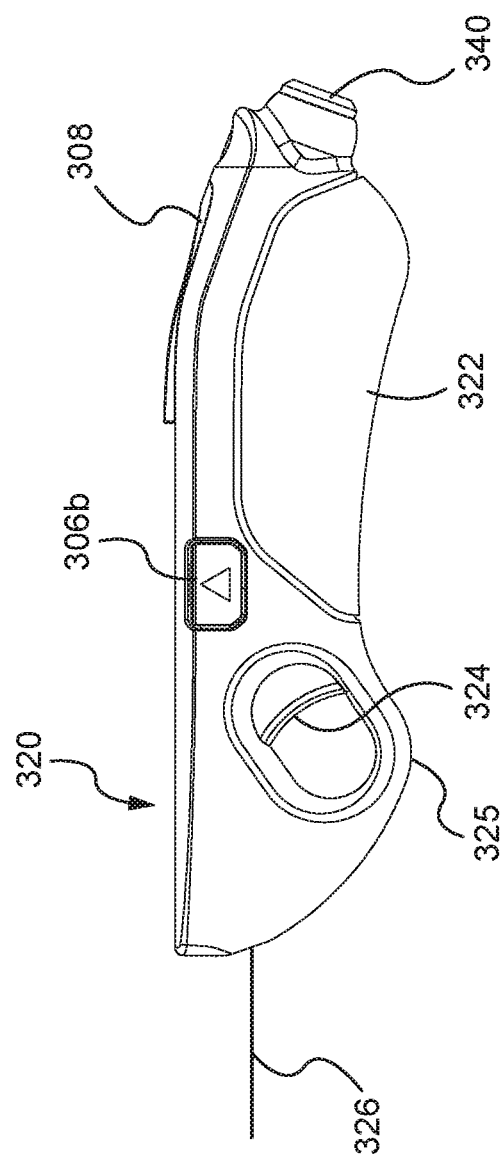
FIG. 17 is a side perspective view of the handle assembly depicted in FIG. 11.

In addition, the cartridge assembly 310 may include a gear locking mechanism, as depicted in FIG. 16. As depicted, the gear locking mechanism includes a linear spring 318 and a gear lock component 319. The gear locking mechanism is designed to lock a position of the drive gear 222 when the cartridge assembly 310 is separated from the handle assembly 320. The spring 318 may push on the gear lock component 319 so that the gear lock component 319 protrudes from a proximal face of the cartridge assembly 310 when the cartridge assembly 310 is not attached to the handle assembly 320 (see FIGS. 13-15). When the gear lock component 319 protrudes outwards, the spring 318 (disposed internally) or an internal portion of the gear lock component 319 may interlock with the drive gear 222 and prevent its rotation. Thus, when a situation occurs that prompts separation of the cartridge assembly 310 from the handle assembly 320, the gear lock mechanism would allow a user to manually rotate the cartridge assembly 310 (and, with it, the catheter assembly 200) to unwind the basket assembly 210 or another portion of the device. The gear lock mechanism prevents the drive gear 222 from rotating or freely spinning, thereby allowing a manual torsion applied by a user to the cartridge assembly 310 to be transmitted through to the catheter assembly 200. Without the gear lock mechanism, when the basket assembly 210 becomes trapped, rotation of the cartridge assembly 310 may result in the drive gear 222 freely spinning within the cartridge assembly 310 rather than transmitting the manual torsion applied by a user to the basket assembly 210. When the cartridge assembly 310 is assembled onto the handle assembly 320, the handle assembly 320 may automatically depress a rear face of the gear lock component 319. In its depressed state, the internal design of the gear lock mechanism may release the drive gear 222, once again allowing it to rotate independently from the cartridge assembly 310.

Figure 12:
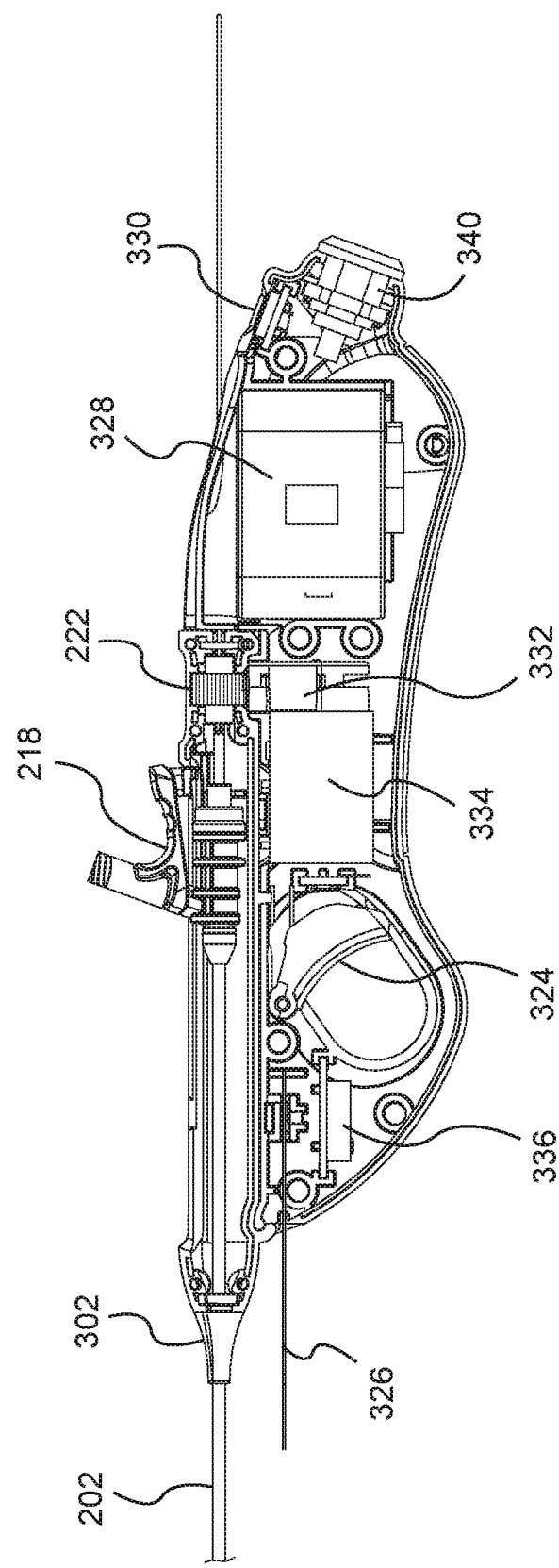
FIG. 12 is a side view of the cartridge assembly and the handle assembly depicted in FIG. 11 with a portion of an outer housing removed to show interior components of the cartridge assembly and the handle assembly.
Figure 13:
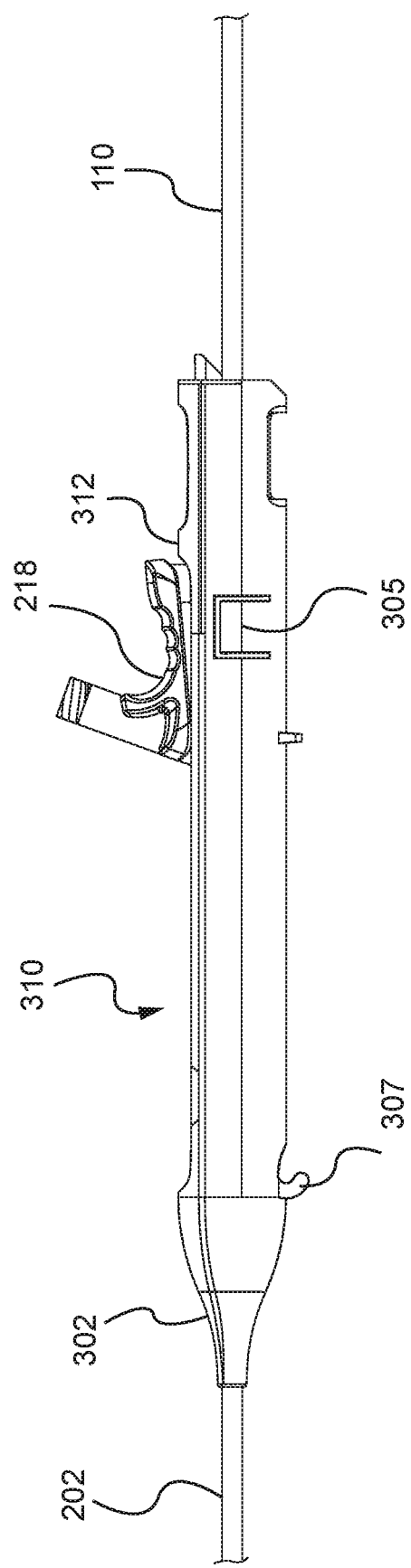
FIG. 13 is a side perspective view of the cartridge assembly depicted in FIG. 11.

Referring again to FIG. 11, the handle assembly 320 includes a battery cover 308, a grip area 322, a trigger 324, and a mechanical interrupt mechanism 326. Additionally, as depicted in FIG. 12, the handle assembly 320 houses a motor 334, a gear box 332, a battery pack 328, and a printed circuit board (PCB) 336. The motor 334, the battery pack 328, and the PCB 336 are connected to one another via an electrical circuit. The electronical circuit may comprise standard wire leads, which come together at the PCB 336. The battery pack 328 includes one or more batteries that supply power to the motor 334. The battery pack 328 may be connected to the electrical wiring of the device via an electrical connector that may be removed by a user.

Access to the battery pack 328 is provided through the battery cover 308. The battery cover 308 may be pivoted upwards to allow a user to insert or remove batteries from the battery pack 328. According to certain aspects of the disclosure, the cartridge assembly 310 covers a portion of the battery cover 308 to prevent the battery cover 308 from opening during a clinical procedure. In such aspects, the cartridge assembly 310 may be removed from the handle assembly 320 in order to provide access to the battery cover 308, and to allow a user to open the battery cover 308 to access the battery pack 328 within the handle assembly 320. The battery cover 308 may be opened by depressing an access tab on the battery cover 308. In certain aspects, the battery cover 308 may also include breakaway tabs that prevent the reassembly of the device (e.g., breakaway tabs that prevent cartridge assembly 310 from reattaching to the handle assembly 320, or breakaway tabs that prevent the battery cover 308 from closing after being pivoted open). Such may be desirable to limit reuse of the device when the device is intended for single use.

The handle assembly 320 may comprise an outer shell that is formed of two housing sections that may be pressed together to form the outer shell. Each housing section may form one half of the outer shell. The two housing sections when pressed together may stay attached to one another through the use of bosses on one section that mates with receiving holes on the other section. The bosses and receiving holes may have an interference or friction fit that allows for easy assembly. The outer shell of the handle assembly 320 may be ergonomically designed. For example, the outer shell of the handle assembly 320 may include a grip area 322 that is ergonomically designed to fit in the palm of a user's hand. The trigger 324 may also be positioned in the handle assembly 320 such that it may be activated by a user using a thumb or index finger. In addition, the handle assembly 320 may include a trigger guard feature 325 that reduces the risk of inadvertent activation of the device, including the basket assembly 210.

The PCB 336 includes a circuit design that is capable of passive switching between a first actuation mechanism and a second actuation mechanism. The first actuation mechanism may be, for example, the trigger 324. The second actuation mechanism may be a foot pedal, such as the foot pedal 400 depicted in FIGS. 18 and 19. The second actuation mechanism may be connected to the handle assembly 320 via a cable that attaches to a connector 340 disposed on the handle assembly 320. As depicted in FIGS. 11 and 12, this connector 340 may be disposed at a rear end of the handle assembly 320. According to an aspect of the disclosure, the end of the cable may comprise a male head, and the connector 340 may be a female connector. When the second actuation mechanism (e.g., the foot pedal 400) is connected to rear of the handle assembly 320, the PCB 336 may detect the second actuation mechanism and bypass the first actuation mechanism. More specifically, when the second actuation mechanism is connected to the handle assembly 320, the circuit design of the PCB 336 may be configured to respond to electrical signals sent by the second actuation mechanism and not those sent by the first actuation mechanism. As such, when the second actuation mechanism is connected, the trigger 324 may become inactive or non-operational. When the second actuation mechanism is disconnected from the handle assembly 320, then the PCB 336 may return control to the trigger 324. Because this switching from the first actuation mechanism to the second and back to the first occurs passively, the device provides ease of use for a user.

The PCB 336 may also include a circuit design that limits the amount of current that is passed to the motor 334. For example, the PCB 336 may include a resistor/capacitor circuit design that disconnects power to the motor 334 (or cuts off the electrical connection to the trigger 324 or another actuation mechanism) when a specific current load threshold is reached for a time exceeding a set point. The current load of the motor 334 may be correlated with an amount of torque that is applied to the basket assembly 210 of the catheter assembly 200. The current load threshold may be set to a value that ensures that the amount of torque that is applied to the basket assembly 210 does not exceed the mechanical strength of the basket components. As such, the PCB 336 may be designed to reduce a risk of damaging or detaching parts of the basket assembly 210 or exacerbating an embolic condition. The handle assembly 320 may further include a reset switch 330. The reset switch 330 may be depressed by a user to reset the circuit such that the trigger 324 or another actuation mechanism may again actuate the motor 334. In particular, the depression of the reset switch 330 may allow charge that has built up in the resistor/capacitor circuit to discharge to once again allow the motor 334 to be actuated. According to certain aspects, the reset switch 330 may be coupled to an indicating light. When the current load threshold is reached, the indicating light may light up to notify a user that the circuit needs to be reset.

The handle assembly 320 may also include a mechanical interrupt mechanism 326 that is capable of interrupting power flow through the device. The mechanism interrupt mechanism 326 may provide safety during sterilization and also ensure that the battery pack 328 does not drain during shipping and storage. The mechanical interrupt mechanism 326 may be removed prior to using the device.

The gear box or gear train 332 of the handle assembly 320 may include a shaft gear and an idler gear. The motor 334, the shaft gear, and the idler gear may be mounted to a single frame (e.g., a motor mount or a box frame). The shaft gear may be connected to a motor shaft of the motor 334. The shaft gear in turn may engage with the idler gear. The gear train 332 including the shaft gear and the idler gear may be enclosed by a gear cover. When the cartridge assembly 310 holding the catheter assembly 200 is attached to the handle assembly 320 (e.g., when the catheter assembly 200, the cartridge assembly 310, and the handle assembly 320 are assembled together), the idler gear may engage with the drive gear 222 of the catheter assembly 200. Then, when the trigger 324 or the foot pedal 400 is activated to actuate the motor 334, the motor 334 may drive the motor shaft, which rotates the shaft gear, which in turn rotates the idler gear, which further in turn rotates the drive gear 222, which translates that rotation to the torque cable 212 and the basket assembly 210. According to certain aspects of the disclosure, the gear train 332 may also include a lesser number or a greater number of gears.

Figure 18:
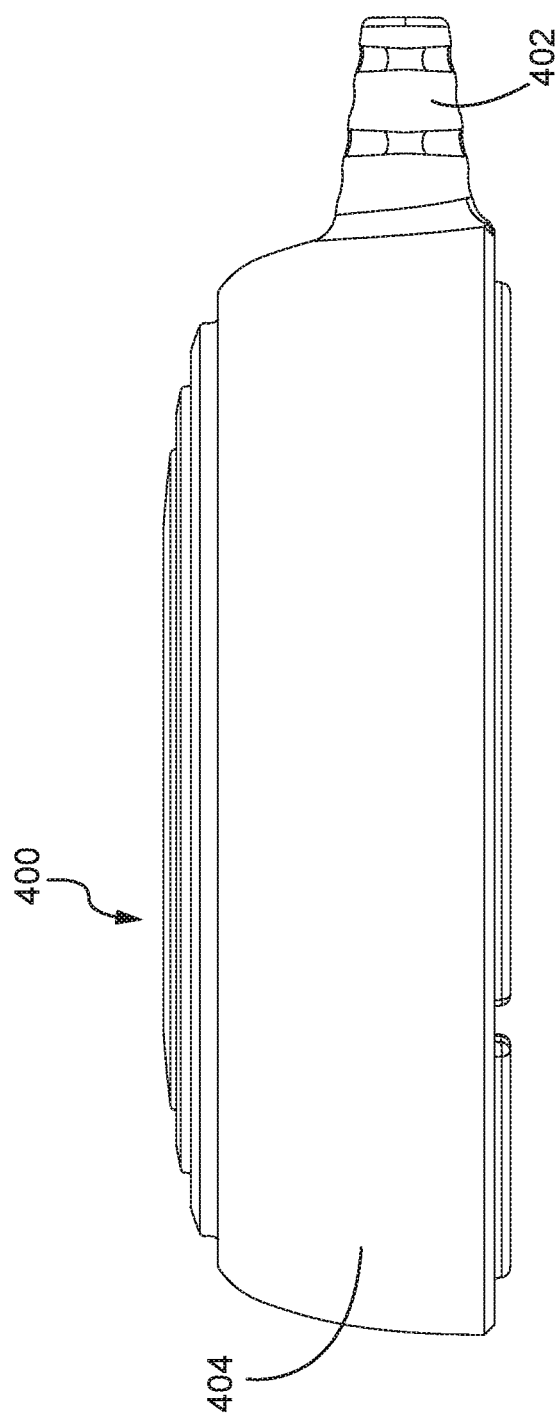
FIG. 18 is a side perspective view of an example foot actuation mechanism according to an aspect of the disclosure.

Referring now to FIG. 18, an example foot pedal 400 is depicted. The foot pedal 400 may be an example of a second actuation mechanism. As described above, the foot pedal 400 may be connected to the handle assembly 320 of the mechanical thrombectomy device 100 via a cable, which plugs into a connector 340 of the handle assembly 320. The cable may extend from a connector 402 disposed on a side of the foot pedal 400. When connected to the handle assembly 320, the foot pedal 400 may provide an alternative method for actuating the motor 334.

Figure 19:
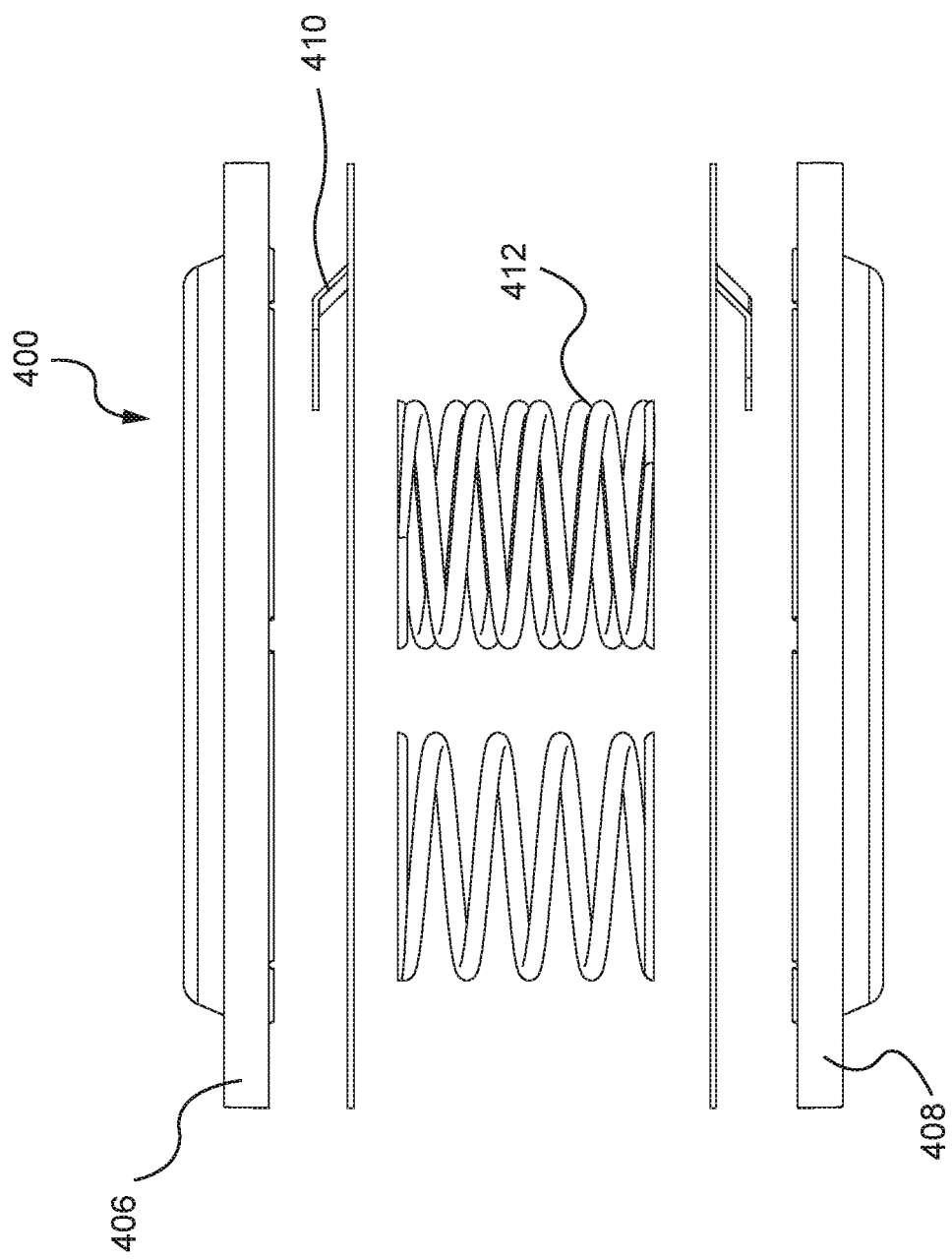
FIG. 19 is a deconstructed view of the example foot actuation mechanism depicted in FIG. 18.

The foot pedal 400 may comprise an outer cover 404 and two plates 406, 408 (see FIG. 19). The outer cover 404 may be an elastomeric cover such as a rubber cover. The two plates 406, 408 may be separated from one another by a plurality of springs. As depicted in FIG. 19, the two plates 406, 408 may be separated from one another by three springs 412. Electrical contacts 410 may be disposed on an inner face of the plates 406, 408. Each electrical contact 410 may be connected to a wire lead that runs through a flexible cord or cable to the handle assembly 320. As described above, the flexible cable may plug into the connector 340 of the handle assembly 320. In an aspect, the electrical contacts may be ring-shaped.

The foot pedal 400 may be activated by depressing the top plate 406 relative to the bottom plate 408. When the top plate 406 is depressed, the electrical contacts 410 may touch one another to close the circuit and actuate the motor 334.

Figure 20:
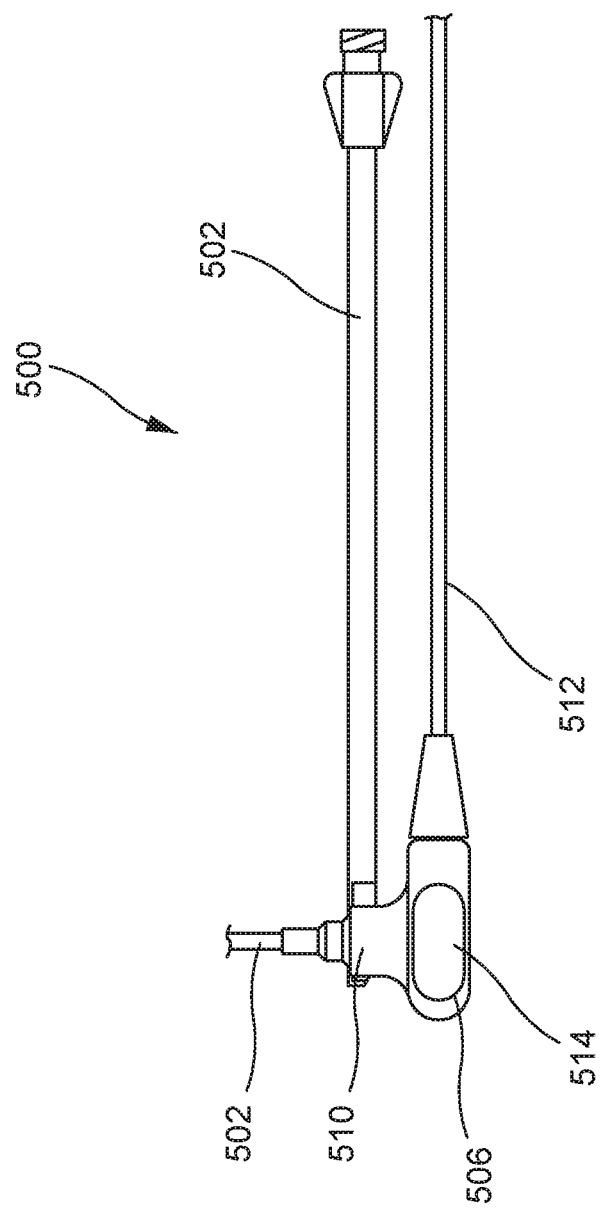
FIG. 20 is a top perspective view of an example hand actuation mechanism according to an aspect of the disclosure.
Figure 21:
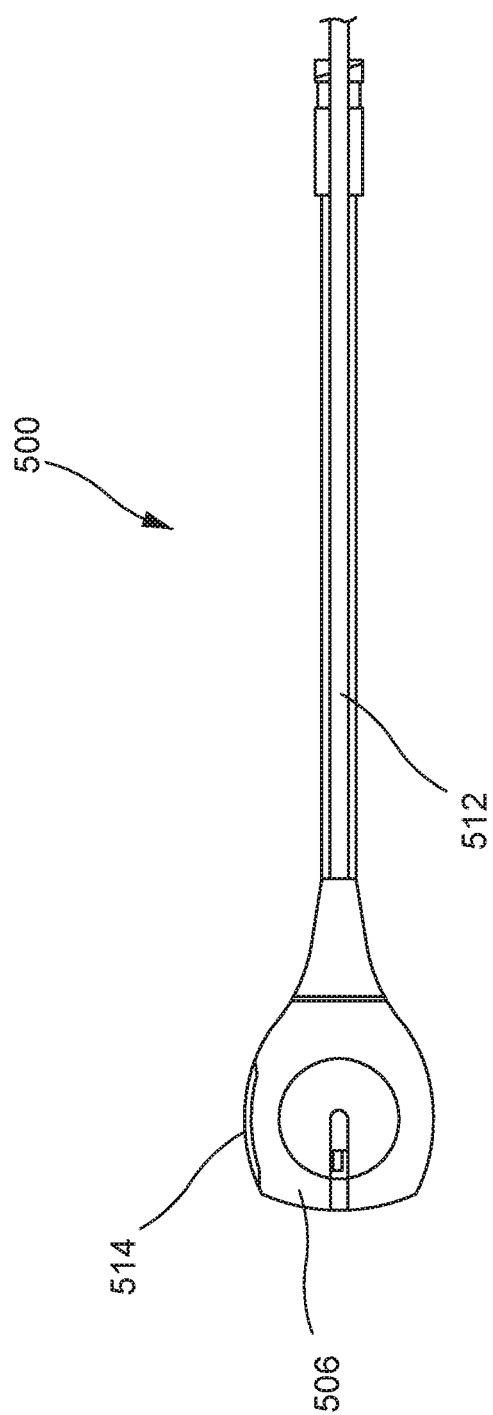
FIG. 21 is a side perspective view of the example hand actuation mechanism depicted in FIG. 20.

Referring now to FIGS. 20 and 21, an example hand-operated actuation mechanism 500 is depicted. The actuation mechanism 500 may be another example of a second actuation mechanism. The actuation mechanism 500 may comprise a clip mechanism 510 that allows it to attach to a proximal end of a catheter assembly. As depicted in FIGS. 20 and 21, the clip mechanism 510 of the actuation mechanism 500 is capable of attaching to the outer surface of an introducer sheath 502. The actuation mechanism 500 further includes a main body 506 with a trigger 514 (e.g., a button). The trigger 514 may be depressed to actuate a motor of a handle assembly, such as the motor 334 of the handle assembly 320. The main body 506 and the trigger 514 may be designed such that the trigger 514 may be depressed by an index finger of a user. According to alternative aspects of the disclosure, the main body 506 and the trigger 514 of the actuation mechanism 500 may be shaped such that the trigger 514 may be depressed by another finger of a user. Such is described with reference to FIGS. 22 and 23, below.

The actuation mechanism 500 may be manipulated by a user using a single hand. The actuation mechanism 500 may be connected to a handle assembly via a cable 512.

Figure 22:
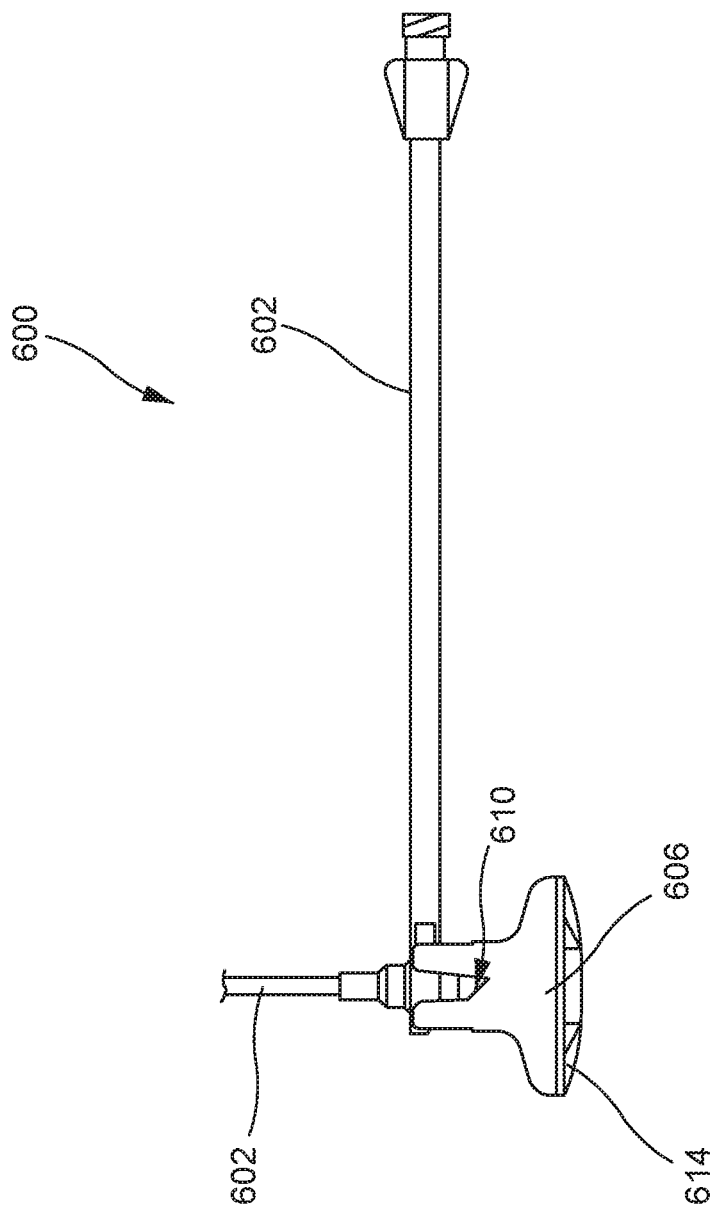
FIG. 22 is a top perspective view of another example hand actuation mechanism according to an aspect of the disclosure.
Figure 23:
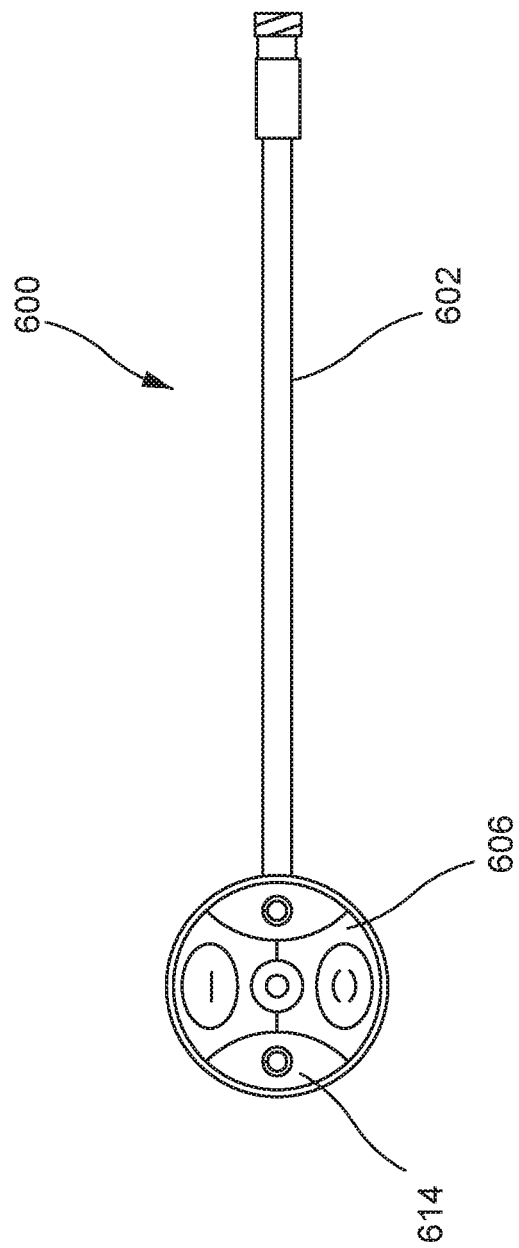
FIG. 23 is a side perspective view of the example hand actuation mechanism depicted in FIG. 22.

Referring now to FIGS. 22 and 23, another example hand-operated actuation mechanism 600 is depicted. The actuation mechanism 600 may be another example of a second actuation mechanism. Similar to the actuation mechanism 500, the actuation mechanism 600 may clip onto a proximal end of a catheter assembly. The actuation mechanism 600 may comprise a plurality of clips or latches 610 that clip onto an introducer sheath 602.

The actuation mechanism 600 may be activated by depressing a trigger 614 on a main body 606 of the actuation mechanism 600. The main body 606 and the trigger 614 may be designed such that the trigger 614 may be depressed by a thumb of a user. Specifically, the main body 606 may be designed to be grasped by one user's hand such that the user's thumb is positioned over the trigger 614. The actuation mechanism 600 may communicate with a handle assembly via wireless communication technology such as, for example, Bluetooth and other near field communication (NFC) technology.

Figure 24:
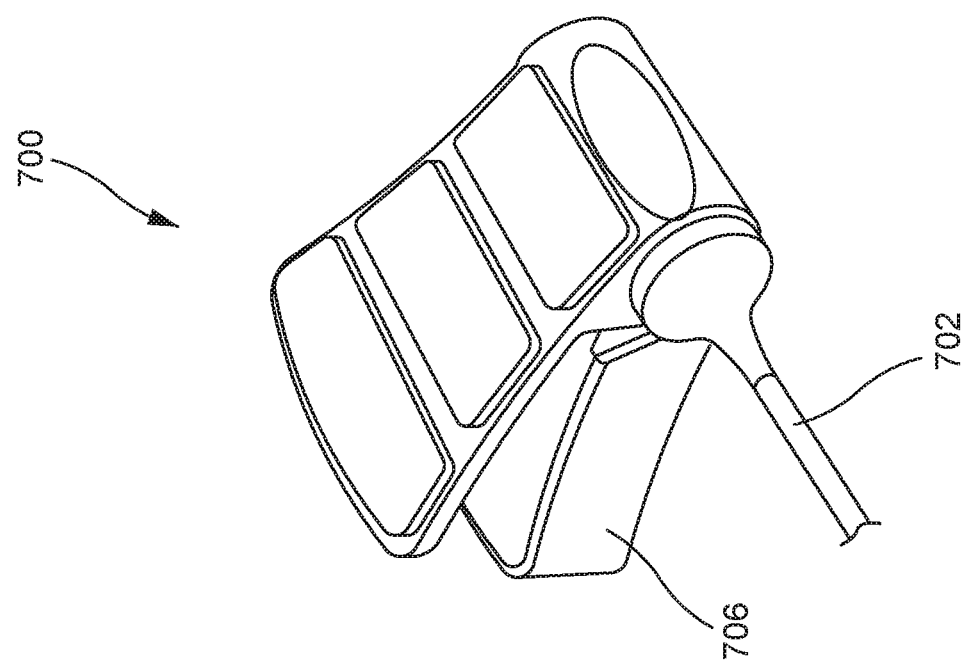
FIG. 24 is a perspective view of another example foot actuation mechanism according to an aspect of the disclosure.

Referring now to FIGS. 24 and 25, an example foot pedal 700 is depicted. The foot pedal 700 may comprise a motor 708 and a battery pack 710 including one or more batteries. The foot pedal 700 may connect to a handle assembly via a cable 702. The cable 702 may include a rotatable shaft that is capable of transmitting a torque from the foot pedal 700 to the handle assembly. The handle assembly may transfer this torque to a torque cable (e.g., the torque cable 212), thereby rotating a basket assembly. According to this configuration where the motor 708 and the battery pack 710 are disposed in the foot pedal 700, the handle assembly may not include an additional motor and battery pack. Accordingly, the handle assembly may be reduced in size, providing for a more streamlined design.

The many features and advantages of a mechanical thrombectomy device described herein are apparent from the detailed specification, and thus, the claims cover all such features and advantages within the scope of this application. Further, numerous modifications and variations are possible. As such, it is not desired to limit the mechanical thrombectomy device to the exact construction and operation described and illustrated and, accordingly, all suitable modifications and equivalents may fall within the scope of the claims.

What is claimed is:

1. A mechanical thrombectomy device, the device comprising:
   a catheter assembly comprising:
      a rotatable shaft having a proximal end and a distal end; and
      a basket assembly attached to the distal end of the rotatable shaft, the basket assembly comprising:
         a proximal hub and a distal hub disposed on a longitudinal axis of the basket assembly;
         a flexible inner tube having a first end attached to the proximal hub and a second end attached to the distal hub; and
         a plurality of basket wires, each of the plurality of basket wires having a first end attached to the proximal hub and a second end attached to the distal hub, the plurality of basket wires disposed around the flexible inner tube, the plurality of basket wires configured to expand to a preset shape; and
   a drive assembly configured to rotate the rotatable shaft, wherein the basket assembly is configured to rotate with the rotatable shaft to macerate a material proximate to the basket assembly, and
   wherein the flexible inner tube comprises a plurality of independent pieces separated by perforations such that the flexible inner tube can bend relative to the longitudinal axis of the basket assembly in the absence of a guidewire when the proximal hub and the distal hub are aligned along the longitudinal axis.

2. The mechanical thrombectomy device of claim 1, further comprising:
   a sheath configured to cover the plurality of basket wires and prevent expansion of the plurality of basket wires; and
   a retracting mechanism attached to a proximal end of the sheath, the retracting mechanism configured to retract the sheath to allow expansion of the plurality of basket wires.

3. The mechanical thrombectomy device of claim 2, further comprising:
   an infusion port for receiving a fluid,
   wherein an outside surface of the rotatable shaft and an inside surface of the sheath define an infusion lumen, and the infusion lumen is configured to deliver the fluid received by the infusion port to a proximity of the material.

4. The mechanical thrombectomy device of claim 1, wherein the drive assembly comprises:
   a motor;
   a first actuation mechanism configured to actuate the motor to rotate the rotatable shaft;
   a battery configured to supply power to the motor; and
   a circuit board.

5. The mechanical thrombectomy device of claim 4, wherein the circuit board is configured to disconnect power to the motor from the battery when a current load of the motor is greater than a predefined threshold value.

6. The mechanical thrombectomy device of claim 5, wherein the drive assembly further comprises a reset switch, and the reset switch is configured to reconnect power to the motor from the battery.

7. The mechanical thrombectomy device of claim 4, wherein the motor, the first actuation mechanism, the battery, and the circuit board are disposed in a handle housing, and the handle housing comprises a grip area having ergonomic features.

8. The mechanical thrombectomy device of claim 7, wherein the handle housing further comprises a trigger guard configured to surround a portion of the first actuation mechanism.

9. The mechanical thrombectomy device of claim 4, wherein the drive assembly further comprises a gear train, the gear train comprising:
   a first gear attached to a motor shaft of the motor; and
   a second gear configured to engage the first gear,
      wherein the motor, the first gear, and the second gear are mounted to a frame, and the motor is configured to rotate the first gear and the second gear.

10. The mechanical thrombectomy device of claim 9, wherein the catheter assembly comprises a third gear, the second gear of the gear train is further configured to engage with the third gear and to rotate the third gear, and the third gear is configured to rotate the rotatable shaft.

11. The mechanical thrombectomy device of claim 10, wherein a proximal end of the catheter assembly is enclosed in a cartridge assembly, the cartridge assembly is detachable from the drive assembly, the cartridge assembly further comprises a locking mechanism, the locking mechanism is configured to lock a position of the third gear when the cartridge assembly is detached from the drive assembly, and the cartridge assembly is configured to transfer a manual rotation of the cartridge assembly to the rotatable shaft when the position of the third gear is locked.

12. The mechanical thrombectomy device of claim 11, wherein the locking mechanism comprises a spring.

13. The mechanical thrombectomy device of claim 1, wherein the plurality of basket wires comprises at least four basket wires.

14. The mechanical thrombectomy device of claim 1, wherein the distal hub of the basket assembly comprises a conical tip.

15. The mechanical thrombectomy device of claim 14, wherein the conical tip comprises at least one of: a cross-cut engraving, a concentric engraving, and a spiral engraving.

16. The mechanical thrombectomy device of claim 1, further comprising a center lumen configured to receive a guidewire, wherein the center lumen extends through an inner lumen of the rotatable shaft and an inner lumen of the flexible inner tube.

17. The mechanical thrombectomy device of claim 1, wherein the perforations of the flexible inner tube form a jigsaw pattern.

18. The mechanical thrombectomy device of claim 1, wherein the flexible inner tube is configured to elongate, to compress, and to rotate.

19. A catheter assembly of a medical thrombectomy device, the catheter assembly comprising:
   a rotatable shaft having a proximal end and a distal end; and
   a basket assembly attached to the distal end of the rotatable shaft, the basket assembly comprising:
      a proximal hub and a distal hub disposed on a longitudinal axis of the basket assembly;
      a flexible inner tube having a first end attached to the proximal hub and a second end attached to the distal hub; and
      a plurality of basket wires, each of the plurality of basket wires having a first end attached to the proximal hub and a second end attached to the distal hub, the plurality of basket wires disposed around the flexible inner tube, the plurality of basket wires configured to expand to a preset shape,
   wherein the basket assembly is configured to rotate to macerate a material proximate to the basket assembly, and
   wherein the flexible inner tube comprises a plurality of independent pieces separated by perforations such that the flexible inner tube can bend relative to the longitudinal axis of the basket assembly in the absence of a guidewire when the proximal hub and the distal hub are aligned along the longitudinal axis.

20. A method of treating thrombosis, comprising:
   inserting a distal end of a catheter assembly into a vasculature, the catheter assembly comprising:
      a rotatable shaft;
      a basket assembly, the basket assembly disposed at the distal end of the catheter assembly, the basket assembly attached to the rotatable shaft, the basket assembly comprising:
         a proximal hub and a distal hub disposed on a longitudinal axis of the basket assembly;
         a flexible inner tube having a first end attached to the proximal hub and a second end attached to the distal hub, the flexible inner tube comprising perforations such that the flexible inner tube and the basket assembly can bend relative to the longitudinal axis of the basket assembly in the absence of a guidewire when the proximal hub and the distal hub are aligned along the longitudinal axis; and
         a plurality of basket wires, each of the plurality of basket wires having a first end attached to the proximal hub and a second end attached to the distal hub, the plurality of basket wires disposed around the flexible inner tube; and
      a sheath covering the plurality of basket wires;
   moving the basket assembly to a predetermined position within the vasculature;
   retracting the sheath to expand the plurality of basket wires to a preset shape; and
   rotating the rotatable shaft to rotate the plurality of basket wires in the expanded state to macerate a material proximate to the basket assembly.

* * * * *